US005800553A

United States Patent [19]
Albrektsson et al.

[11] Patent Number: 5,800,553
[45] Date of Patent: Sep. 1, 1998

[54] HIP JOINT PROSTHESIS TO BE PERMANENTLY ANCHORED WITHIN A FEMUR OF A PATIENT

[75] Inventors: Bjorn Albrektsson, Onsala; Magnus Jacobsson, Goteborg; Lars Carlsson; Tord Rostlund, both of Kullavik; Stig Wennberg, Angered, all of Sweden

[73] Assignee: Aktiebolaget Astra, Sweden

[21] Appl. No.: 185,814

[22] PCT Filed: Jul. 4, 1992

[86] PCT No.: PCT/SE92/00511

§ 371 Date: May 2, 1994

§ 102(e) Date: May 2, 1994

[87] PCT Pub. No.: WO93/01769

PCT Pub. Date: Feb. 4, 1993

[30] Foreign Application Priority Data

Jul. 23, 1991 [SE] Sweden ................... 9102216

[51] Int. Cl.$^6$ ........................................ A61F 2/36
[52] U.S. Cl. ................................. 623/23; 606/65
[58] Field of Search ......................... 623/23, 16, 18, 623/22, 19; 606/65, 66, 63

[56] References Cited

U.S. PATENT DOCUMENTS

| | | | |
|---|---|---|---|
| 2,381,050 | 8/1945 | Hardinge | 606/65 |
| 2,397,545 | 4/1946 | Hardinge | 606/65 |
| 2,612,159 | 9/1952 | Collison . | |
| 3,102,536 | 9/1963 | Rose et al. | 623/23 X |
| 3,806,957 | 4/1974 | Shersher | 623/23 |
| 3,987,499 | 10/1976 | Scharbach et al. | 606/61 X |
| 4,129,903 | 12/1978 | Huggler | 623/23 |
| 4,187,559 | 2/1980 | Grell et al. | 623/18 |
| 4,268,919 | 5/1981 | Zeibig | 623/18 |
| 4,388,921 | 6/1983 | Sutter et al. | 411/537 X |
| 4,409,974 | 10/1983 | Freedland | 606/232 X |
| 4,621,629 | 11/1986 | Koeneman | 606/65 |
| 4,795,473 | 1/1989 | Grimes . | |
| 4,878,916 | 11/1989 | Rhenter et al. | 623/18 |
| 5,007,935 | 4/1991 | Vincent et al. | 623/22 |
| 5,074,879 | 12/1991 | Pappas et al. | 623/18 |
| 5,087,260 | 2/1992 | Fixel | 606/65 |

FOREIGN PATENT DOCUMENTS

| | | | |
|---|---|---|---|
| 0515003 | 11/1992 | European Pat. Off. | 623/23 |
| 2438470 | 10/1978 | France . | |
| 2578739 | 9/1986 | France | 623/19 |
| 2646478 | 10/1976 | Germany . | |
| 2724234 | 5/1977 | Germany . | |
| 2854334 | 6/1980 | Germany | 623/23 |
| 3607824 | 3/1986 | Germany . | |
| 3917285 | 11/1990 | Germany | 623/19 |
| 3921030 | 1/1991 | Germany | 623/16 |
| 0602171 | 4/1978 | U.S.S.R. | 606/65 |
| 2166359 | 11/1984 | United Kingdom . | |
| 8603962 | 7/1986 | WIPO | 623/23 |
| WO8911837 | 12/1989 | WIPO . | |

*Primary Examiner*—David H. Willse
*Attorney, Agent, or Firm*—White & Case

[57] ABSTRACT

A hip joint prosthesis to be permanently anchored in a patient's hip is disclosed. The prosthesis comprises an attachment part for a ball unit designed to be anchored in the neck of a human femur. The attachment part comprises a primary fixture which may be an elongate anchoring element which is intended to be inserted into a channel extending through the femoral collum. The prosthesis also includes a secondary fixture for carrying a ball intended to be attached to the collum after removal of the head of the collum. The primary fixture and the secondary fixture are connected to each other. The prosthesis is preferably designed so that the length of the primary fixture terminates close to the head of the collum. The secondary fixture preferably comprises a plug-like part which is intended to be inserted in a cylindrical countersunk recess that is cut into the cancellous bone of the collum and which extends to the cortical bone in at least three locations.

12 Claims, 8 Drawing Sheets

HIP JOINT PROSTHESIS TO BE PERMANENTLY ANCHORED WITHIN A FEMUR OF A PATIENT

TECHNICAL FIELD OF THE INVENTION

The present invention relates to a hip joint prosthesis intended to be permanently anchored in the human hip joint and more specifically to the part of the hip prosthesis which is to be anchored in the femur or thigh bone of the patient and which comprises an attachment part for a ball unit designed to be anchored in the neck of a human femur (collum femoris), said attachment part comprising an elongate anchoring element or primary fixture intended to be inserted into a channel bored and extending through the femoral collum from the outside of the femur, and a secondary fixture intended to be attached to the collum after removal of the head of the collum, said primary fixture and said secondary fixture being provided with means for connecting said fixtures to each other.

BACKGROUND OF THE INVENTION

The present invention is a development of a hip joint prosthesis of the kind disclosed in WO 89/11837. This document thus inter alia discloses a hip joint prosthesis comprising a primary fixture in the shape of a sleeve, said sleeve being intended to be inserted into a central hole bored longitudinally through the collum femoris from the outer side of the femur and a secondary fixture in the shape of a cap having a spherical shape intended to be attached to and cover the end of the collum femoris when the head of the collum has been removed partly or entirely and the outside of remaining end has been cut to a cylindrical shape. The primary and the secondary fixtures are interconnected by means of a bolt which at one end has an internal thread. The bolt is to be inserted into the sleeve and its internal thread is to be made to engage a central, threaded stud projecting from the spherical cap. When the bolt is tightened, the cap is pressed over the cylindrically cut shape of the end of the collum.

In some applications it is however not suitable to use this prior art device. One reason for this is that the shape of the collum may make it difficult to retain enough cortical bone to give the secondary fixture or cap a firm support, since the shape of the collum may vary greatly. Another reason is that it in some cases may be important to achieve an exactly defined compression of the cortical bone, i. e. that a clearly defined pressure is exerted onto the collum from the secondary fixture irrespective of how the secondary fixture is attached to the primary fixture.

Other similar prior art is disclosed for instance in DE-A1-28 45 231, DE-A1-27 24 040, U.S. Pat. No. 4,795,473 and U.S. Pat. No. 4,005,495.

BRIEF DESCRIPTION OF THE INVENTIVE CONCEPT

According to the invention a hip joint prosthesis of the kind described above is designed with the length of said primary fixture being chosen such that said primary fixture ends close to the head of the collum, said secondary fixture comprising a plug-like part intended to be inserted in a cylindrical countersunk cavity cut into the cancellous bone of the collum and extending to the cortical bone in at least three locations, the size of the secondary fixture being chosen such that the fixture abuts the cortical bone of the collum in at least said three locations.

This will entail that the cortical bone will remain intact to a larger degree and that the load conditions will be such that a physiologically appropriate load on the upper part of the collum can be achieved. Forces can be transferred without any noticeable movements between the implant (secondary fixture) by means of the direct bone contact on the inside of the cortical bone in the collum.

The expansion bolt, which is an preferred embodiment of the means for attaching the primary fixture to the secondary fixture, will also ensure that the primary fixture, which mainly will be located in the cancellous bone in the collum and which therefore may sag to some extent in the above prior art device, is supported in a better way along its longitudinal extent by the secondary fixture. The expansion bolt will also give a connection which is so stiff that fretting corrosion between the parts can be avoided.

DETAILED DESCRIPTION OF A PREFERRED EMBODIMENT OF THE INVENTION

Figures 1, 2:
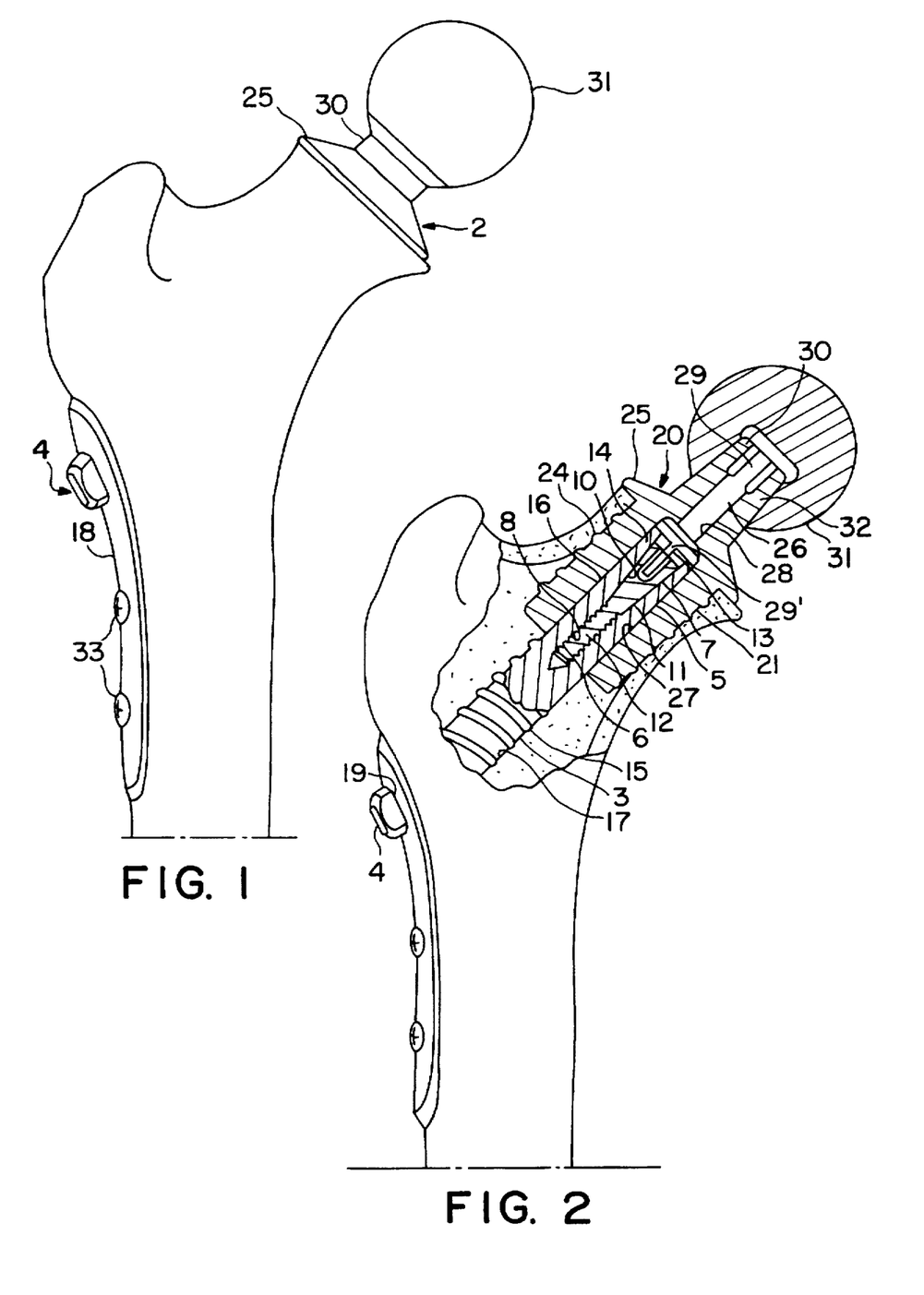
FIG. 1 illustrates a femur with the primary and the secondary fixture mounted, seen from the outside.
FIG. 2 shows the same view as FIG. 1, but partly sectioned.

In FIGS. 1 and 2, which illustrate the prosthetic hip joint in an implanted state, 1 designates the primary fixture and 2 designates the secondary fixture. The primary fixture is in the form of a cylindrical main bolt 3 having a head 4, which preferably has a square shape, and a tubular end part 5 with a longitudinal bore. The tubular part 5 comprises an inner bore part 6 and and an outer bore part 7. The inner part 6 is provided with internal threads 8. The outer part 7 is provided with at least two longitudinal slits 9,9'. The inside 10 of the outer part 7 flares conically outwards. The internal threads 8 and the conically flaring part 10 are complementary to an attachment screw or bolt 11 having an externally threaded end part 12, a head 13 and a shaft 14 tapering conically from the head 13 towards the threaded part 12. The attachment bolt 11 is in engagement with the internal threads of the main bolt 3.

The main bolt 3 is provided with relatively large and widely spaced threads 15 on a part of its outside, the remainder 16 of its outside, substantially corresponding to the outer part 7, being smooth. This smooth part is covered by a plastic layer or by another equivalent coating. The bolt 3 is inserted in a channel 17 bored longitudinally and centrally through the collum 18 from the outside of the femur towards the head of the collum. The head 4 of the main bolt 3 is located on the outside of the femur and is locked against rotation by means of an elongate plate 18 having a hole 19 with a shape complementary to the shape of the head 4 of the main bolt 3. The elongate plate is attached to the femoral shaft by means of screws 33.

The secondary fixture 2 is in the shape of a cylindrical plug 20. One part 21 of the plug 20 is inserted into a recess 22 cut in the collum, cylindrically and co-axially with the channel 17. The outside of this part 21 of the plug preferably is provided with threads 24 similar to the threads 15 on the main bolt 3, except on the part which is located innermost in the recess. The plug 20 also is provided with a circumferential flange 25 limiting the insertion of the plug 20 into the cavity 22. The plug 20 further is provided with a central through-hole 26 having two parts, an inner part 27 having an inner diameter corresponding to the outer diameter of the smooth part 16 of the bolt 3 and an outer part 28 permitting the insertion of a screw-driver or a similar tool for engaging the head of the attachment screw. The outer end of the through-hole is provided with a hexagonal shape 29 for engagement with a suitable hex-tool. The plug finally is provided with a conical projection or attachment cone 30 for carrying the ball or caput 31 which is provided with a complementary conical hole 32.

The primary and the secondary fixtures are preferably made of c.p. (commercially pure) titanium and may be subjected to a suitable surface treatment. The elongate plate 18 preferably is made of a suitable titanium alloy, whereas its attachment screws 33 preferably should be made of c.p. titanium and for instance have a diameter of 4.5 mm. The attachment cone can be made of a titanium alloy or of c.p. titanium and should be treated in a suitable way to minimize the risk for fretting corrosion. The caput preferably should be made of a ceramic material, also in order to minimize the risk for fretting corrosion.

The socket or acetabulum is not part of the present invention and may be of any commerciably available kind which is suitable.

Figure 4:
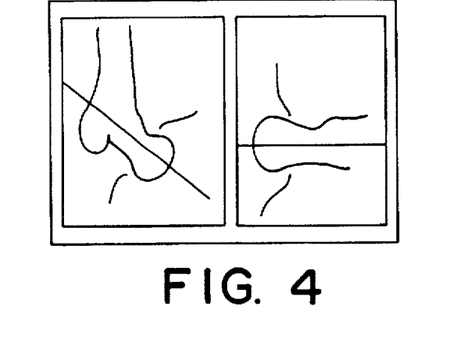
Figure 5:
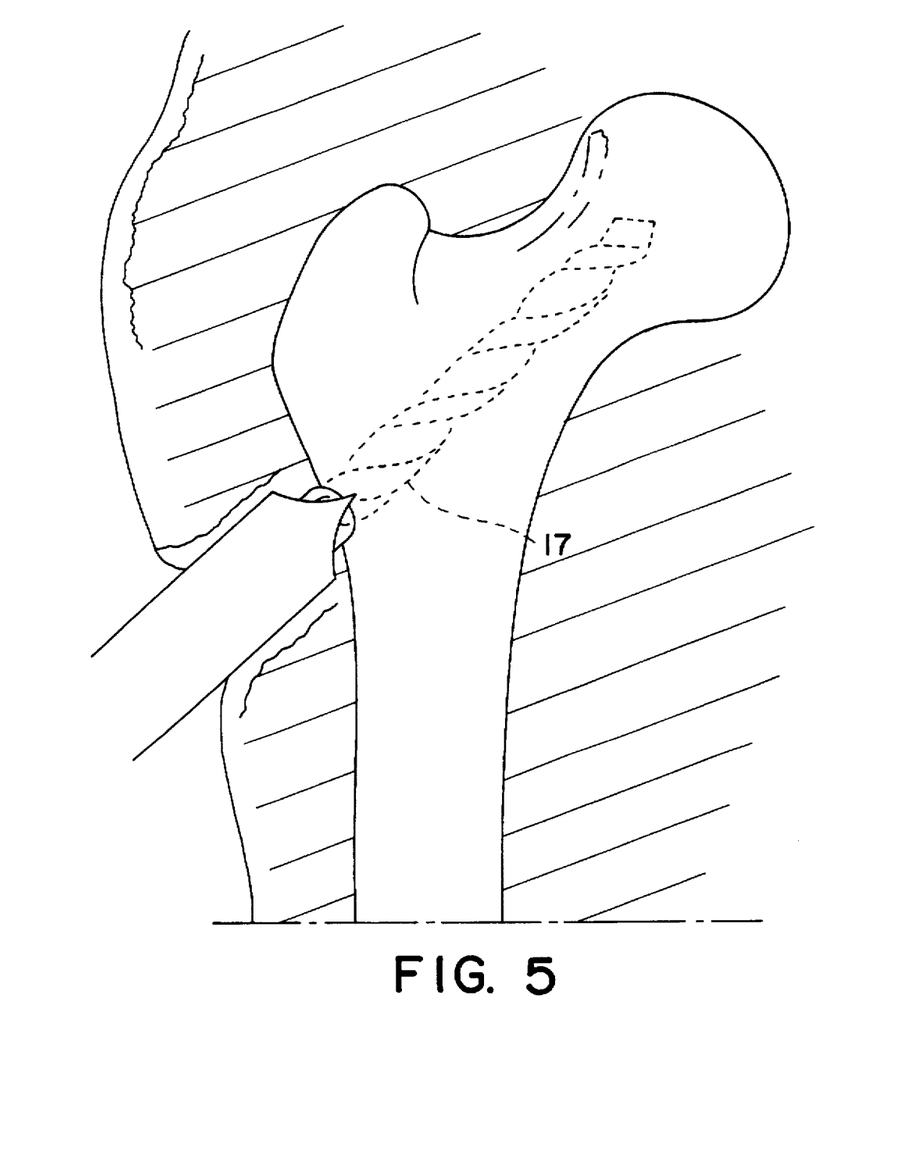
Figure 6:
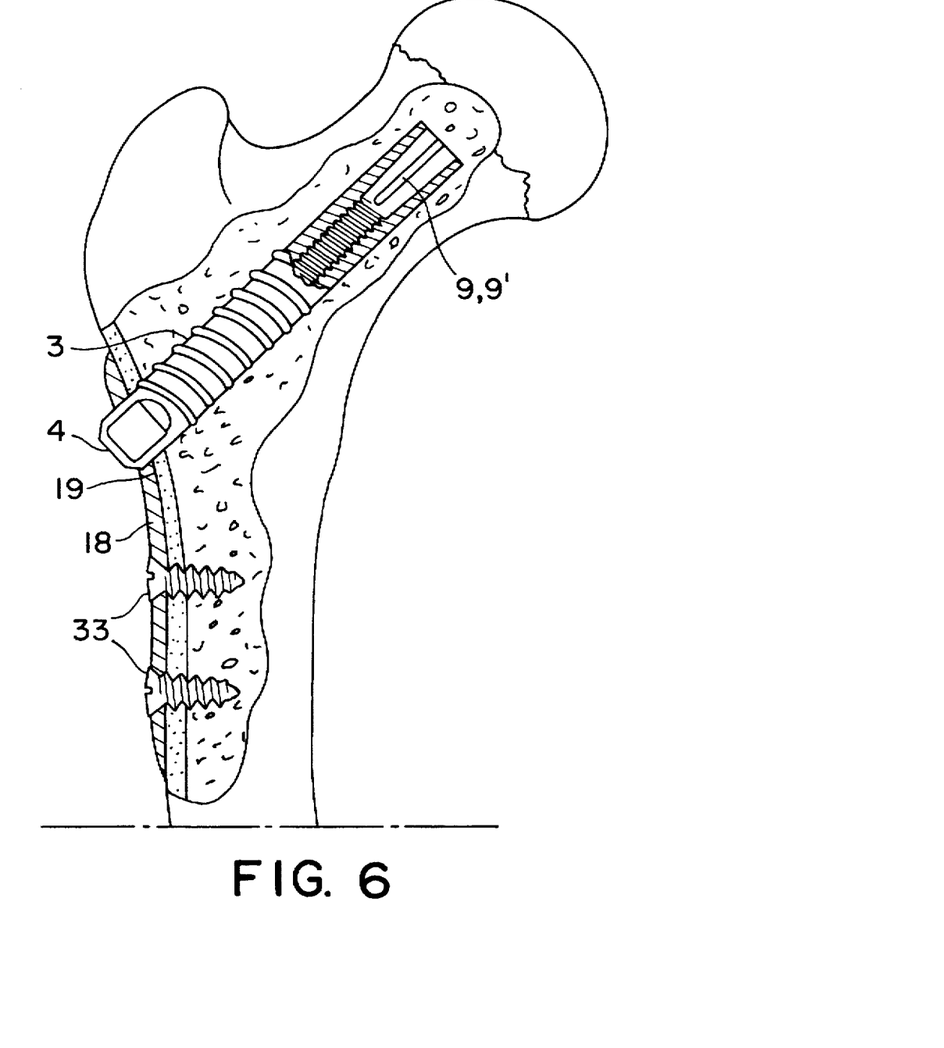

The operation for implanting the hip joint prosthesis is preferably performed in two different stages (but may of course also be performed as a one-stage operation). The preoperative stage of the two-stage operation is illustrated in FIGS. 3 and 4, the first stage of the operation is illustrated in FIGS. 5 and 6 and the final, second stage of the operation is illustrated in FIGS. 7 to 12.

Figure 3:
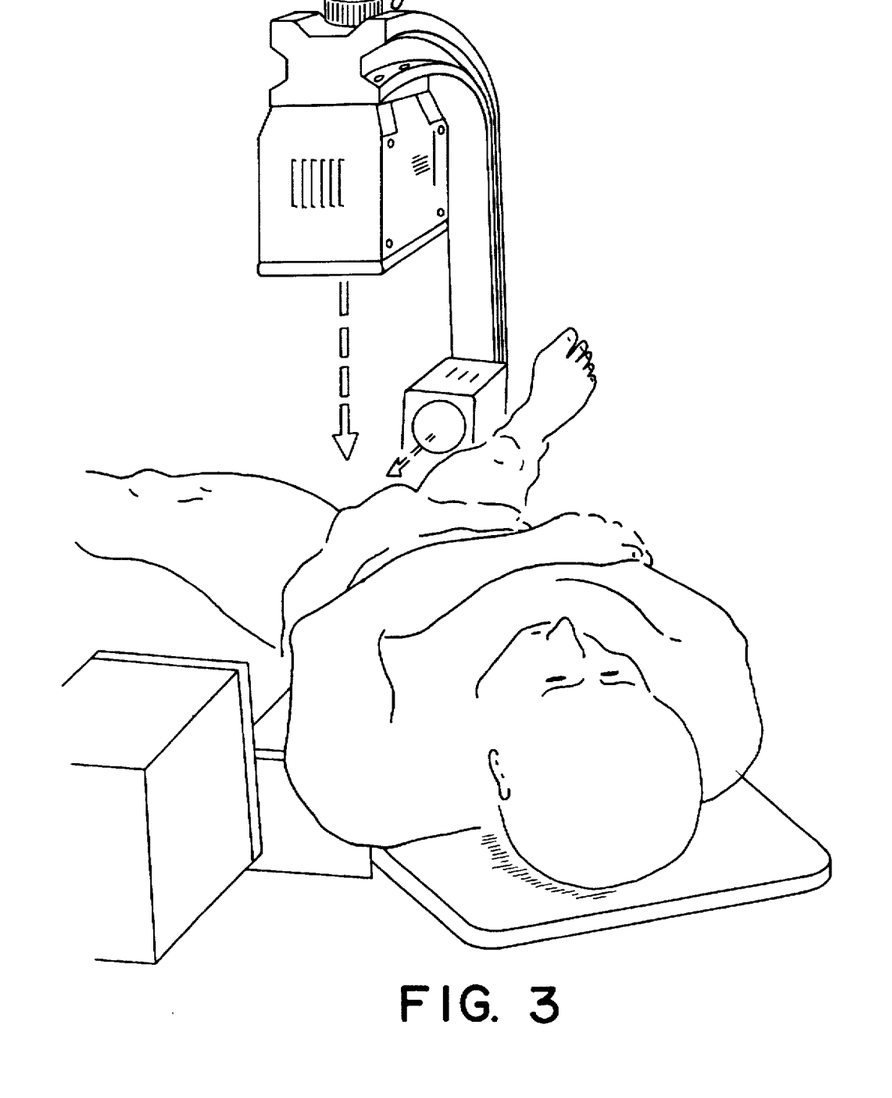
FIGS. 3–12 illustrate the different stages of an operation for implanting the prosthesis.

FIG. 3 shows an X-ray apparatus used in the pre-operative stage and its orientation relative to the patient. Two pictures are taken in orthogonal directions. A suitable length for the primary fixture and a suitable orientation thereof relative to the femoral shaft and the collum femoris is measured on the X-ray pictures, as illustrated in FIG. 4. Any differences in the length of the legs are measured. An estimate of the narrowest diameter of the collum is made in order to obtain an idea of the size of the implant to be used.

In the first stage of the operation the patient lies on a traction table with a bi-planar X-ray apparatus. The pictures are displayed on a video monitor. The femur is rotated inwardly about 20 degrees in order to cancel the angle of anteroversion. When the X-ray apparatus and the display have been adjusted correctly, the position of the primary fixture is marked on both the video displays in accordance with the results obtained from the pre-operative stage. By means of a lateral incision in the skin the outer side of the femur is uncovered. By means of the X-ray display the exact point of entrance for the primary fixture is determined. Thereafter a "Kirchner"-wire or guiding pin provided with threads is bored longitudinally through the collum from the outside of the femur under continuous X-ray control on the video display in order to obtain a central guide pin. The guide pin is bored through the caput and into the acetabulum in order to obtain a temporary fixation of the femur during the remainder of the first stage of the operation. A drill guide is then aligned with the guide pin and is locked by means of an external fixture. A channel 17 is drilled along the guide pin to the depth determined in the pre-operative stage by means of a cannulated drill bit, this part of the operation being carefully cooled and being controlled on the X-ray display, cf FIG. 5.

Interior threads are then cut in the channel 17 by means of a screw tap or similar, the primary fixture 3 is screwed into the channel 17 and the guide pin is removed. The head 4 of the primary fixture 3 is locked laterally against rotation by means of the elongate plate 18 which in turn is fixed against the femoral shaft by means of the two screws 33, cf FIG. 6. The primary fixture may of course also be self-tapping.

The primary fixture 3 is left to heal into the bone tissue or osseointegrate in the collum during 3–6 months. It should be noted that, as mentioned above, the inner end of the primary fixture is covered by a plastic sleeve in order to prevent bone ingrowth.

It should further be noted that both the caput and the acetabulum essentially remain intact and serviceable to the extent existing before the operation during the entire healing time, which is an important advantage of the two-stage operation.

Figure 7:
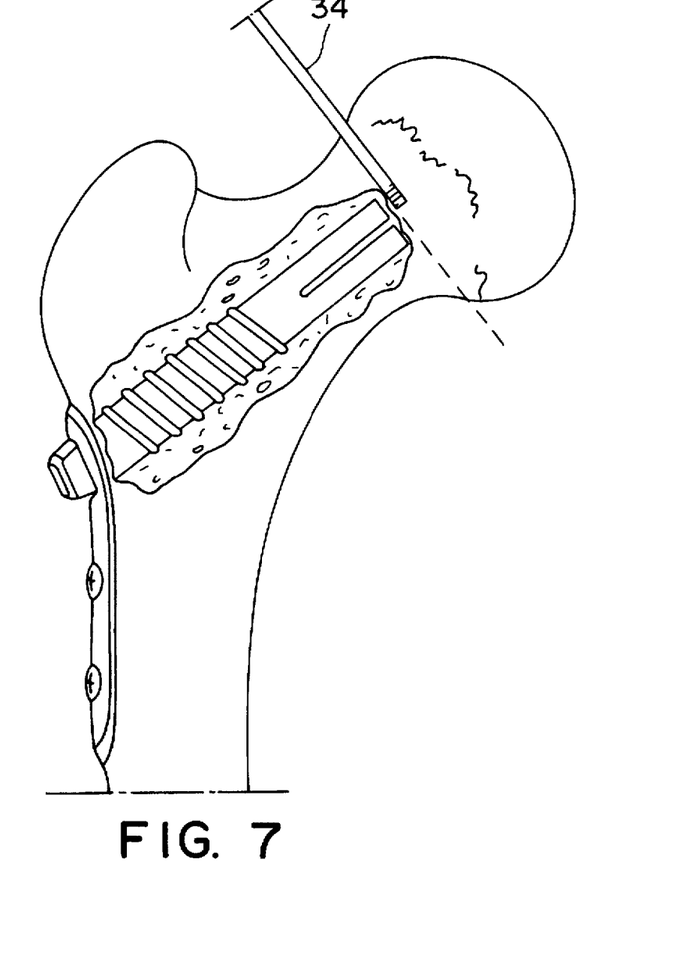

In the second stage of the operation the patient is lying on the side. The hip joint is dislocated. A guide fixture for a cutting tool 34 is attached, for instance to the implanted primary fixture 3, and aligned with the inner end of the primary fixture 3. The caput is then cut close the the inner end of the primary fixture and removed (FIG. 7).

Figures 8, 9:
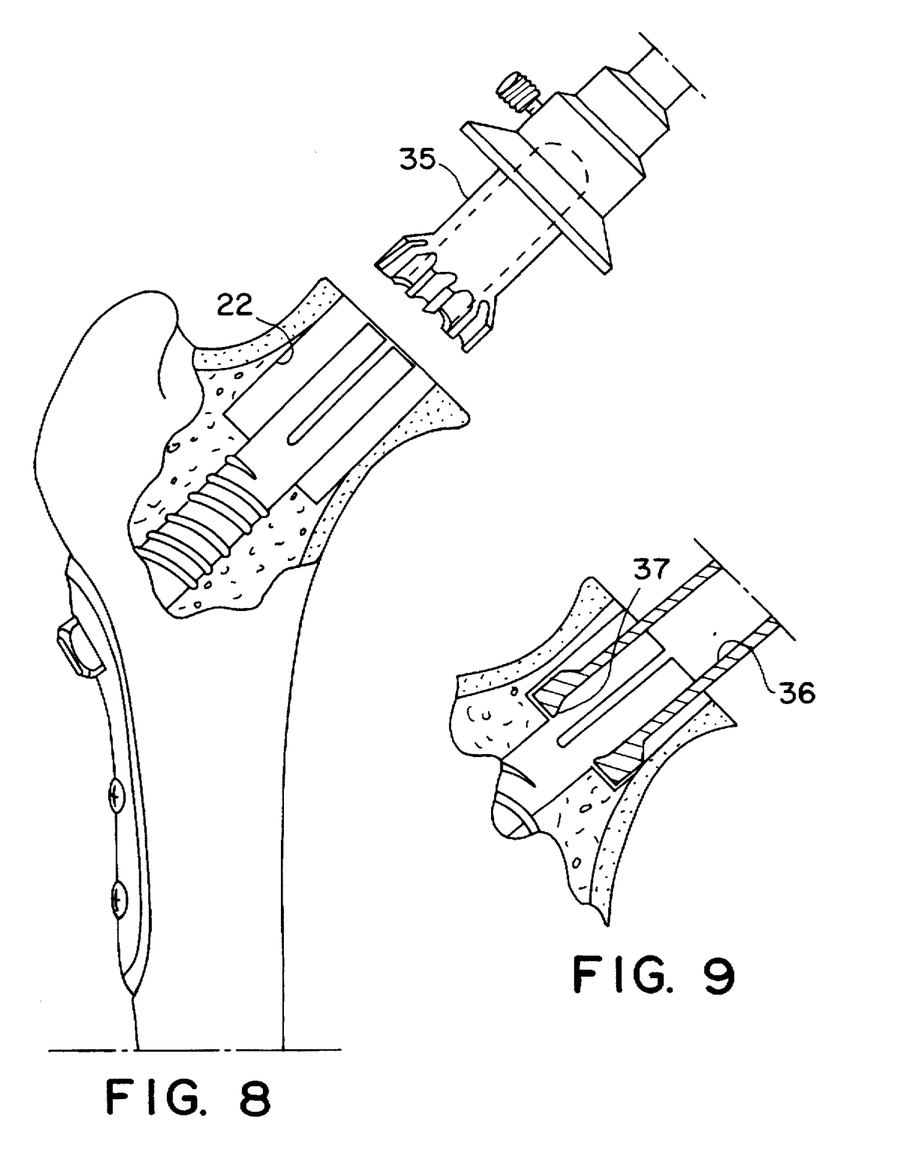

The narrowest part of the collum is measured directly in order to obtain further information regarding the size of the implant. A cylindrical recess or hole 22 is then cut longitudinally in the collum from the direction of the caput by means of a rotary cutting (milling) tool 35 having a longitudinal interior bore 36 which extends from the cutting surface and which has an inner diameter slightly larger than the diameter of the inner end of the primary fixture 3. The edge of the bore 36 should be provided with an interior circumferential rounded bead 37 and the smallest inner diameter of the bore at the bead should be close to the diameter of the inner end of the primary fixture. In this way the primary fixture can be, and is to be, used as a guide for the cutting tool. The circumferential bead is important since it allows smaller misalignments of the cutting tool. Without the bead such misalignments might subject the primary fixture, which as mentioned above mainly is located in the comparatively soft cancellous bone, to unduly large forces. A series of cutting tools with increasing diameters are used successively until the cortical bone is uncovered in at least three locations spaced around the periphery of the inside of the collum. Each cutting tool is corresponds to one size of a secondary fixture (FIGS. 8 and 9).

Threads are cut into the bone tissue on the inside of the recess 22 in the collum. The attachment bolt 11 is inserted into the tubular end of the primary fixture and a secondary fixture having a fitting size is screwed into the recess 22 in the collum, using the primary fixture 3 as a guide, until the flange 25 abuts the cortical bone on the cut end surface of the collum. The unthreaded part on the tip of the secondary fixture will aid in guiding the secondary fixture into the recess 22, cf FIG. 10. The secondary fixture may of course also be self-tapping.

Figures 10, 11:
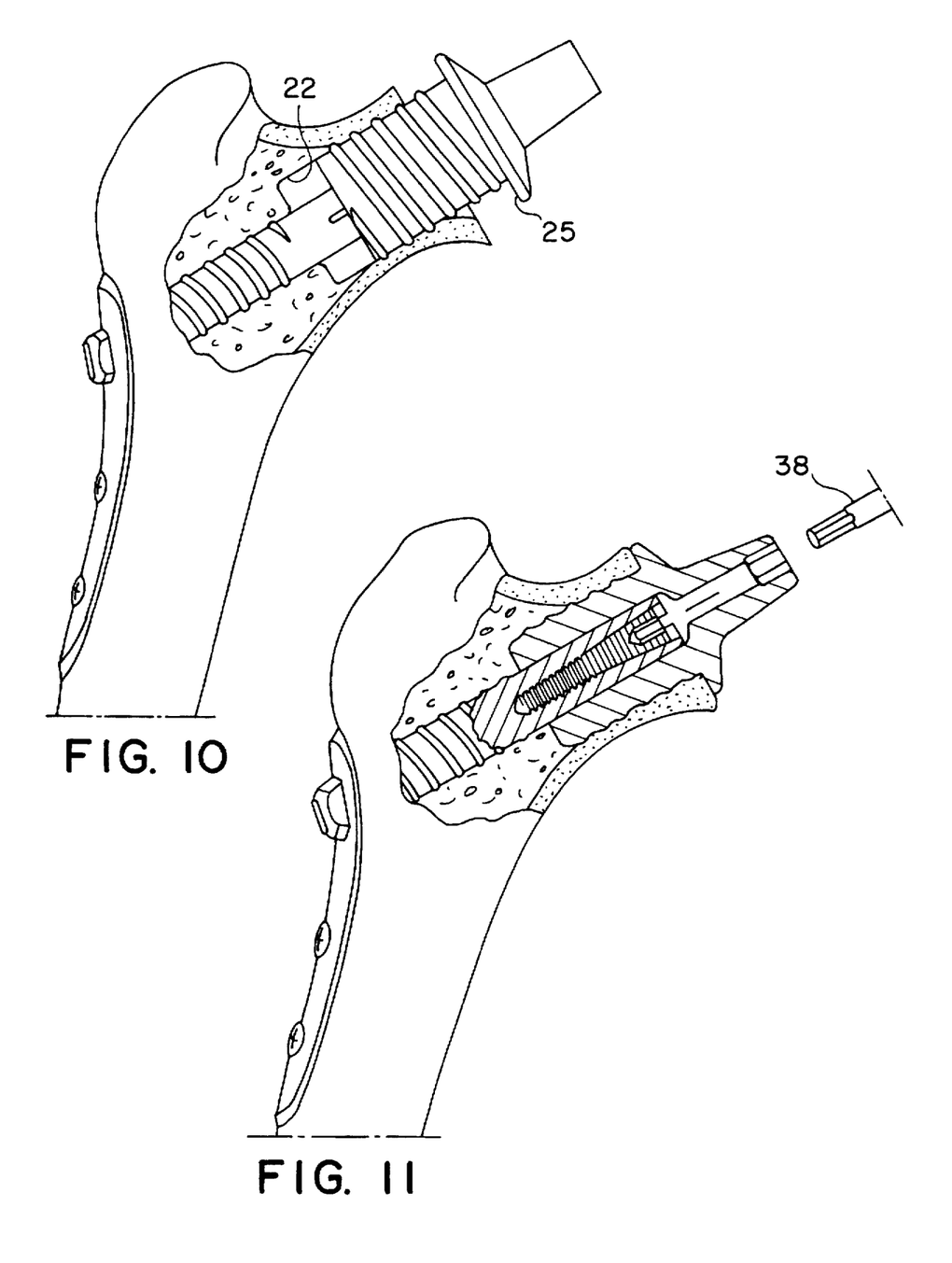

A screw-driver 38 is then inserted into the central through-hole 28 in the secondary fixture and the bolt 11 is tightened, resulting in that the walls of the hollow, conically flaring part of the primary fixture are expanded against the inside of the secondary fixture. This will give a strong and stiff attachment of the secondary fixture to the primary fixture.

This means that the secondary fixture can be tightened with an exact torque, should this be necessary, since the tightening of the bolt 11 not will influence this torque. Sometimes it may also be necessary to leave a small distance between the flange and the collum, which means that the torque should be zero. These are important aspects of the invention.

Finally a ball or caput 31 is mounted on the attachment cone 30 and a reduction or repositioning of the joint is made in order to test the stability of the joint and the length of the leg. The length of the leg is corrected by using caputs having differently sized conical holes 32.

Figure 12:
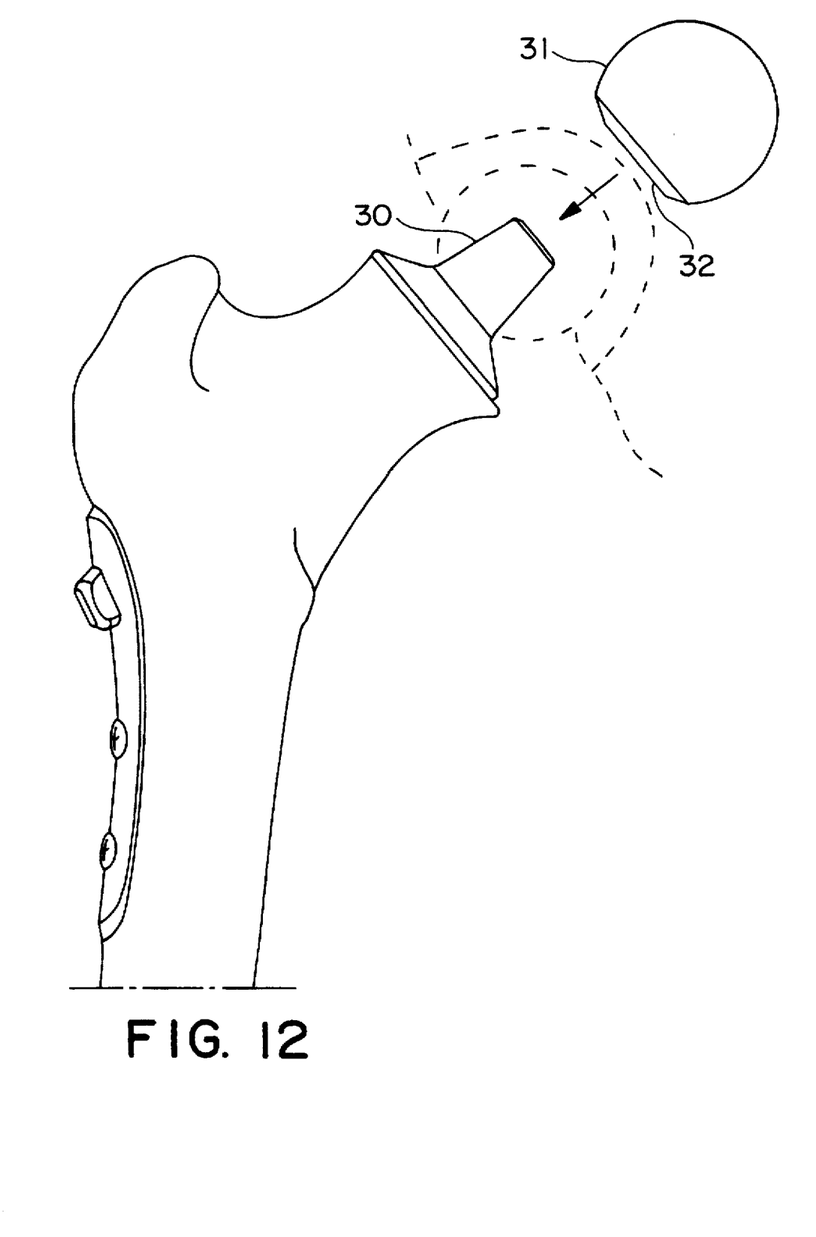

The operation is then completed (FIG. 12).

The invention of course can be varied in many ways within the scope of the appended claims.

We claim:

1. A fixture for a hip joint prosthesis adapted in use to be permanently anchored in a channel provided in a human femur which extends forwardly into the femur neck from an opening in a femur neck section exposed by resection of the femur head towards a position below the greater trochanter of the femur and comprising a rearward section which extends forwardly from the opening and transversely to the outer surface layer of cortical bone of the femur in at least three locations and a co-axial forward section which extends forwardly from the rearward section, the fixture comprising:

a rearward fixture component part for anchorage in the rearward section of the channel which is of such transverse dimensions as to extend to at least three cortical bone locations when anchored in the rearward section of the channel; and a forward fixture component part for anchorage in the forward section of the channel;

wherein a forward end of the rearward fixture component part and a rearward end of the forward fixture component part are adapted to interlock when the fixture component parts are anchored in their respective sections of the channel and wherein securing means are provided for biasing the interlocking end of one of the fixture component parts transversely against the interlocking end of the other fixture component part to secure the forward and rearward fixture component parts together when the fixture component parts are anchored in their respective sections of the channel.

2. The fixture according to claim 1, wherein a recess is provided in the forward end of the rearward fixture component part for receipt of the rearward end of the forward fixture component part and wherein the securing means is adapted to bias the rearward end of the forward fixture component part transversely against a boundary wall of the recess when the fixture component parts are anchored in their respective sections of the channel.

3. The fixture according to claim 2, wherein the recess in the forward end of the rearward fixture component part is a first recess, wherein a second recess is provided in the rearward end of the forward fixture component part and wherein the securing means comprises a securing element which is adapted to be received in the second recess and to act on a boundary wall of the second recess so as to bias the rearward end of the forward fixture component part transversely against the boundary wall of the first recess when the fixture component parts are anchored in their respective sections of the channel.

4. The fixture according to claim 3, wherein the second recess comprises a rearward section which flares inwardly in the forward direction, wherein the securing element comprises a rearward section which flares inwardly in the forward direction for co-operation with the rearward section of the second recess such that displacement of the securing element in the forward direction causes the rearward section of the securing element to apply a transverse force on the boundary wall of the rearward section of the second recess which biases the rearward end of the forward fixture component part transversely against the boundary wall of the first recess when the fixture component parts are anchored in their respective sections of the channel.

5. The fixture according to claim 4, wherein the first recess is a forward section of a through bore provided in the rearward fixture component part and aligned with the second recess whereby access is provided to the securing element to displace the securing element forwardly when the forward and rearward fixture component parts are anchored in their respective sections of the channel.

6. The fixture according to claim 4 or 5, wherein at least two slits are provided in the rearward section of the second recess, the slits extending forwardly from the opening of the second recess and transversely from the boundary wall of the rearward section of the second recess to a outer surface of the forward fixture component part.

7. The fixture according to claim 4 or 5, wherein the second recess further comprises a threaded forward section and the securing element comprises a threaded forward section for co-operation with the threaded forward section of the second recess.

8. The fixture according to claim 1, wherein a rearward end of rearward fixture component part is adapted for carrying a ball unit of the hip joint prosthesis.

9. The fixture according to claim 1, wherein the rearward fixture component part has a transverse dimension which is greater than that of the forward fixture component part.

10. The fixture according to claim 1, wherein the forward and rearward fixture component parts are provided with an external screw thread profile adapted to register in the bone tissue presenting the boundary wall of the channel when the fixture component parts are anchored in their respective sections of the channel.

11. The fixture according to claim 1, wherein the opening of the channel in the femur neck section is a first opening, wherein the channel extends forwardly from the first opening to a second opening positioned below the greater trochanter and a forward end of the forward fixture component part is adapted to project forwardly from the second opening when anchored in the forward section of the channel.

12. A hip joint prosthesis including a femur fixture according to claim 1.

* * * * *

UNITED STATES PATENT AND TRADEMARK OFFICE
CERTIFICATE OF CORRECTION

PATENT NO. : 5,800,553
DATED : September 1, 1998
INVENTOR(S) : Albrektsson et al.

It is certified that error appears in the above-indentified patent and that said Letters Patent is hereby corrected as shown below: On the title page, Item [73], In the assignee, before "Sweden" insert --Sodertalje--.

Col. 5, line 26, claim 1, before"at" insert --the--.

Col. 6, line 6, claim 4, after "direction" delete the comma and insert --and--.

Col. 6, line 28, claim 5, change "a" to --an--.

Col. 6, line 36, claim 8, before "rearward" insert --the--.

Col. 6, line 43, claim 10, before "bone" delete "the".

Col. 6, line 44, claim 10, before "boundary" change "the" to --a--.

Signed and Sealed this

Sixth Day of July, 1999

*Attest:*

Q. TODD DICKINSON

*Attesting Officer*    *Acting Commissioner of Patents and Trademarks*